United States Patent
Fernandez et al.

(10) Patent No.: US 6,911,048 B2
(45) Date of Patent: Jun. 28, 2005

(54) MODULAR HIP PROSTHESIS

(75) Inventors: Jose Fernandez, Gainesville, FL (US); Gary J. Miller, Gainesville, FL (US); C. Michael Mauldin, Lake City, FL (US)

(73) Assignee: Exactech, Inc., Gainesville, FL (US)

( * ) Notice: Subject to any disclaimer, the term of this patent is extended or adjusted under 35 U.S.C. 154(b) by 171 days.

(21) Appl. No.: 10/004,207

(22) Filed: Nov. 1, 2001

(65) Prior Publication Data

US 2002/0038148 A1 Mar. 28, 2002

Related U.S. Application Data

(63) Continuation of application No. 09/524,341, filed on Mar. 13, 2000, now Pat. No. 6,319,286.

(51) Int. Cl.$^7$ ................................................. A61B 2/32
(52) U.S. Cl. .................................................... 623/23.18
(58) Field of Search ........................... 623/16.11, 22.11, 623/23.11, 23.15, 23.19, 23.21, 23.22, 23.24, 23.26, 23.29, 23.31, 23.35

(56) References Cited

U.S. PATENT DOCUMENTS

| | | | | | |
|---|---|---|---|---|---|
| 5,002,578 A | * | 3/1991 | Luman | ...................... | 623/22.42 |
| 5,156,627 A | * | 10/1992 | Amstutz et al. | .......... | 623/22.41 |
| 5,368,881 A | * | 11/1994 | Kelman et al. | ............. | 427/2.26 |
| 5,858,020 A | * | 1/1999 | Johnson et al. | ........... | 623/23.15 |
| 5,876,459 A | * | 3/1999 | Powell | ...................... | 623/23.15 |
| 5,902,340 A | * | 5/1999 | White et al. | ................. | 128/898 |
| 5,972,032 A | * | 10/1999 | Lopez et al. | .............. | 623/22.32 |
| 6,190,417 B1 | * | 2/2001 | Itoman et al. | ............ | 623/23.15 |
| 6,200,349 B1 | * | 3/2001 | Naybour | ................... | 623/23.15 |
| 6,319,286 B1 | * | 11/2001 | Fernandez et al. | ........ | 623/23.18 |
| 6,428,578 B2 | * | 8/2002 | White | ....................... | 623/23.22 |

FOREIGN PATENT DOCUMENTS

| | | | | | |
|---|---|---|---|---|---|
| DE | WO 96/15739 | * | 5/1996 | ............. | A61F/2/36 |

* cited by examiner

*Primary Examiner*—Eduardo C. Robert
*Assistant Examiner*—Michael B. Priddy
(74) *Attorney, Agent, or Firm*—Greenberg Traurig LLP

(57) ABSTRACT

A modular hip prosthesis, comprising: (a) a proximal segment including a neck lockingly engageable with a femoral head component and a male tapered portion; (b) a distal segment having a proximal end and a distal tip, the distal segment further formed with a male tapered portion adjacent the proximal end thereof; and (c) a metaphyseal segment having a proximal end and a distal end, the metaphyseal segment preferably including a bone engaging outer surface portion, and further including an axial bore therethrough, the axial bore including first and second female tapered portions formed adjacent the proximal and distal ends thereof, respectively. The first female tapered portion of the metaphyseal segment is dimensionally configured to lockingly engage the male tapered portion of the proximal segment. The second female tapered portion of the metaphyseal segment is dimensionally configured to lockingly engage the male tapered portion of the distal segment. Optionally, a screw dimensionally configured to pass through aligned bores in the proximal, metaphyseal and distal segments is threadably engaged with a threaded bore formed in the proximal end of the distal segment.

27 Claims, 7 Drawing Sheets

MODULAR HIP PROSTHESIS

RELATED APPLICATION

This application is a Continuation application of U.S. Ser. No. 09/524,341, filed Mar. 13, 2000 now U.S. Pat. No. 6,319,286.

BACKGROUND AND SUMMARY OF THE INVENTION

The present invention relates generally to the field of total hip arthroplasty, and, more particularly, to a three segment modular hip stem that allows full size interchangeability between component parts, yet provides superior resistance to component disengagement during use.

Modularity in total hip arthroplasty design is an evolving concept that is receiving increased citation in the clinical literature. The advantages of these systems include off the shelf flexibility for customizing proximal and distal canal filling, as well as accommodating difficult situations of proximal deformity and bone loss. These designs, however, raise concerns that include structural compromise at the metal-metal interconnections due to stresses and intercomponent disengagement.

To address these concerns, the present invention, in summary, provides a modular hip prosthesis comprising the following components: (a) a proximal segment having an axial bore therethrough, the proximal segment including a neck lockingly engageable with a femoral head component, and further including a male tapered portion extending distally of said neck; (b) a distal segment having a proximal end and a distal tip, the distal segment further being formed with a male tapered portion adjacent the proximal end thereof; and (c) a metaphyseal segment having a proximal end and a distal end, the metaphyseal segment including a bone engaging outer surface portion, and further including an axial bore therethrough, the axial bore including first and second female tapered portions, the first female tapered portion located adjacent the proximal end of the metaphyseal segment and dimensionally configured to lockingly engage the male tapered portion of the proximal segment, the second female tapered section located adjacent the distal end of the metaphyseal segment and dimensionally configured to lockingly engage the male tapered portion of the distal segment.

The male and female tapered portions of the corresponding proximal, metaphyseal and distal segments each comprises a conical section blending into a generally parabolic-shaped section. The blended conical taper/parabolic taper geometry of each tapered portion ensures sufficient taper contact area, and decreases the interfacial contact stresses and internal body stresses under bending loading of the male/female taper junction. The conical tapered sections each have taper angles ranging from about 1° to about 2.5° to provide enhanced torsional resistance at the taper junctions. The proximal segment is lockingly engageable with the proximal end of the metaphyseal segment to align the axial bores formed through the proximal and metaphyseal segments. The proximal end of the distal segment is lockingly engageable with the distal end of the metaphyseal segment to align the axial bores formed through the distal and metaphyseal segments.

Optionally, the proximal segment is formed with a throughbore, and the distal segment is formed with a threaded bore adjacent the proximal end thereof. These bores are alignable with the axial bore of the metaphyseal segment. A screw, dimensionally configured to pass through the aligned bores, is threadably engaged with the threaded bore formed in the distal segment to further enhance locking engagement of the prosthesis components if desired.

The present invention provides the following advantages: (a) superior resistance to component disassociation by increasing taper contact area and reducing contact stresses due to bending and torsional loads at the taper junctions; (b) intraoperative flexibility through its modularity; (c) full interchangeability of any segment with any other segment; (d) adjustability of each segment for anteversion and retroversion independent of the position of other segments, thus allowing a universal design for left and right hip applications; (e) independent selection of leg length and offset of the prosthesis; (f) primary and revision application with the same system; (g) allows the surgeon to tailor the device to the anatomy of the patient even in the face of a revision surgery that might leave a bone deficit; and (h) the use of all styles and sizes of femoral head components.

The accompanying drawings, which are incorporated in and constitute part of the specification, illustrate the detailed description and preferred embodiments of the invention, and together with the detailed description, serve to explain the principles of the invention. It is to be understood, however, that both the drawings and the description are explanatory only and are not restrictive of the invention.

DETAILED DESCRIPTION OF THE INVENTION

Figure 1:
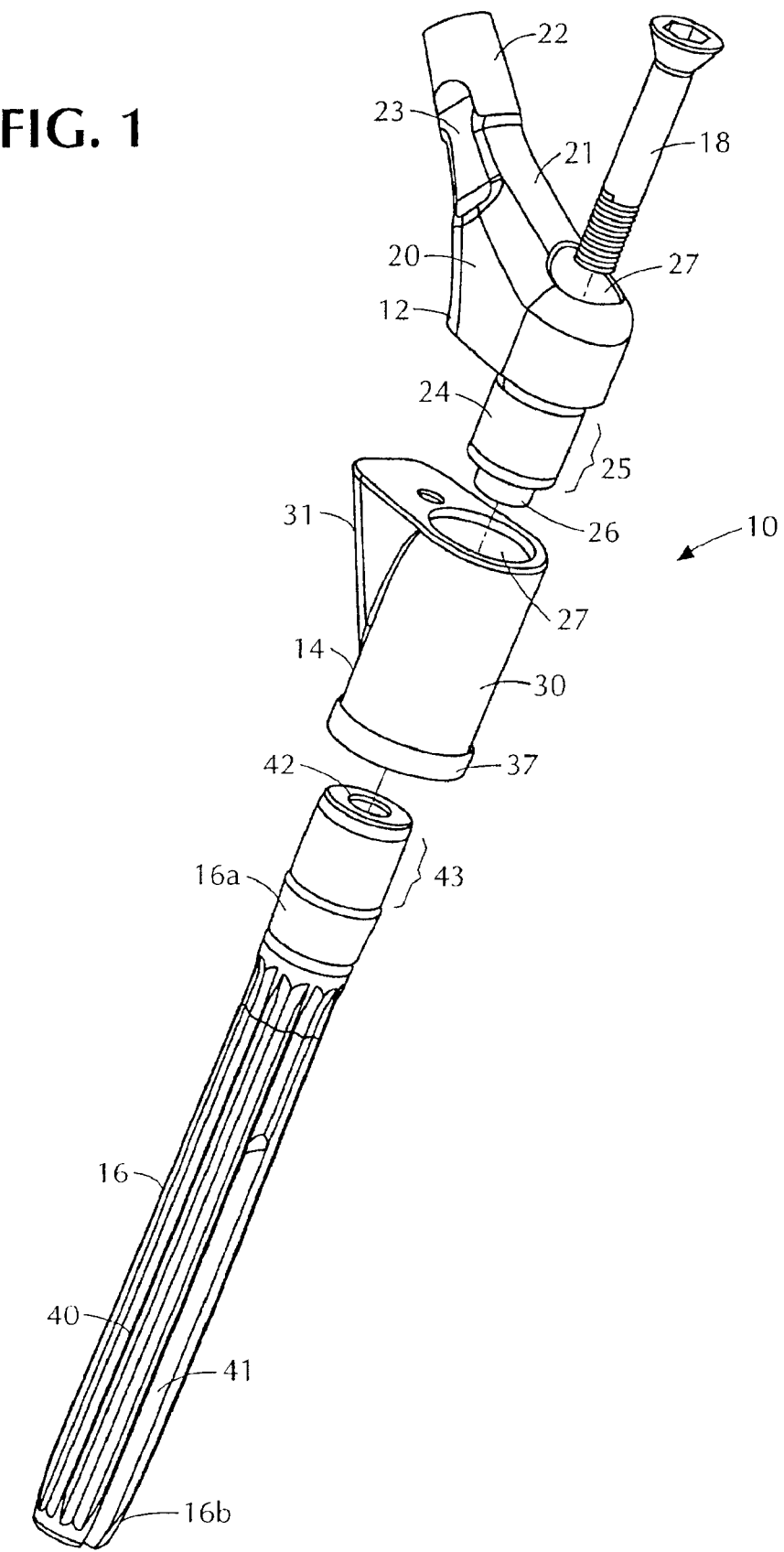
FIG. 1 is an exploded, perspective view of one embodiment of the modular hip prosthesis of the invention.

Referring now to FIGS. 1–8, wherein like reference numerals are used to identify like components throughout the various views, a first embodiment of the modular hip prosthesis of the invention is shown generally at 10. As shown in FIG. 1, hip prosthesis 10 generally includes: (a) a proximal segment 12; (b) a metaphyseal segment 14; and (c) a distal segment 16. A threaded screw 18 may optionally be used to enhance locking engagement of segments 12, 14, and 16 as described below. As here embodied, proximal segment 12, metaphyseal segment 14, and distal segment 16 are each constructed as separate parts. As a result, the segments may each be sized independently of one another. Such independent sizing capability gives the prosthesis modularity—that is, it provides the surgeon with a wide selection of prosthesis configurations to accommodate virtually every anatomical condition encountered during surgery. Advantageously, the modular prosthesis 10 of the invention may be implanted using well known bone cement implantation techniques, or, in the alternative, may be implanted in an uncemented mode, using bone engaging surface applications well known to persons skilled in the art.

Figure 2:
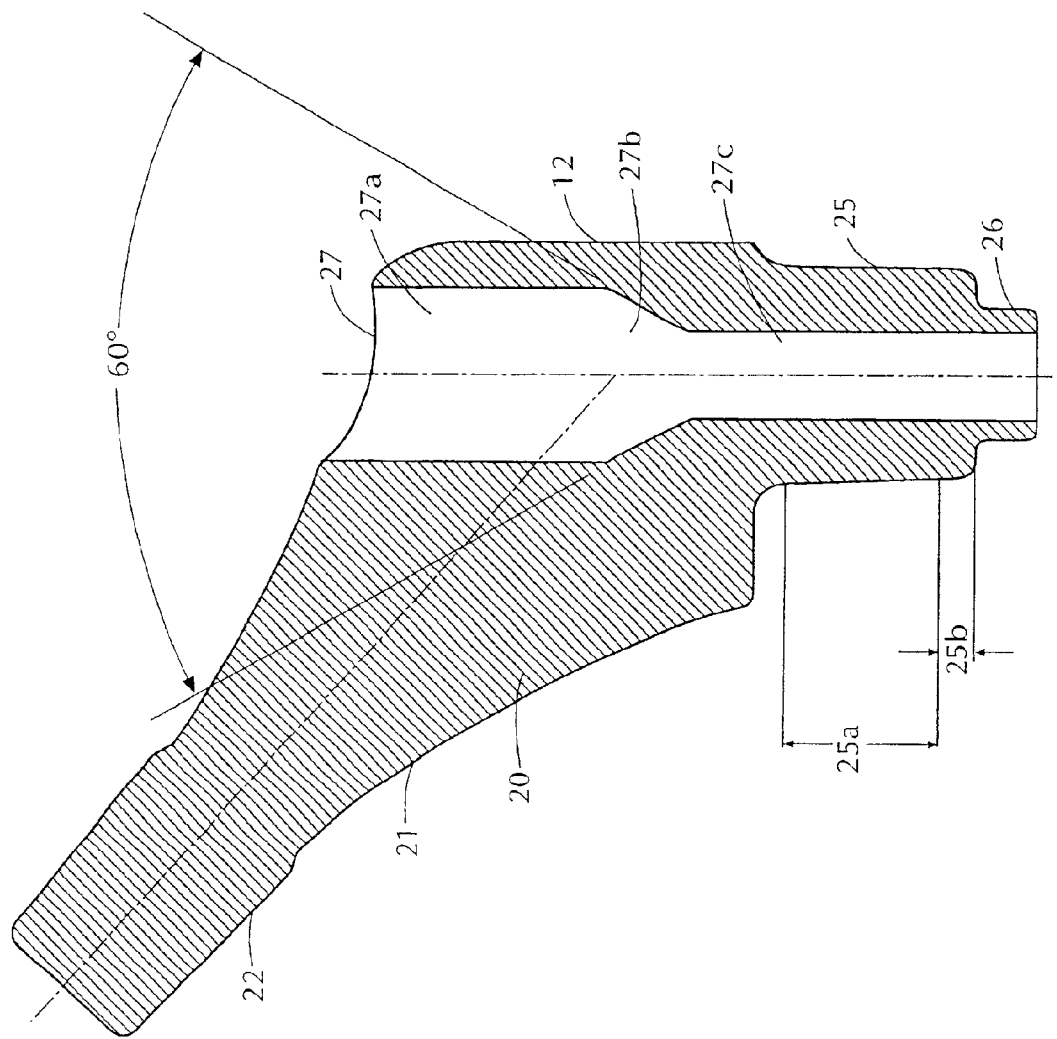
FIG. 2 is a cross-sectional, side elevation view of one embodiment of the proximal component of the invention.

Referring now to FIG. 2, proximal segment 12 includes a neck 20 formed with: (a) an angularly offset arm 21 terminating in a male tapered column 22; (b) an extension member 24 extending distally of neck 20 formed with a male tapered portion 25, and terminating in a cylindrical nipple 26; and (c) a segmented bore 27 formed through neck 20, extension member 24, and nipple 26. Preferably, proximal segment 12 is constructed from a biocompatible, high strength titanium alloy. However, proximal segment 12 may be constructed from other biocompatible materials such as cobalt chromium alloy, stainless steel, and composite materials. The outer surface finish of proximal segment 12 is preferably polished, with a surface roughness average of 32 microinches or less as determined by profilometry. The outer surface finish may also be smooth matte or machined using surface preparation techniques well known in the art.

Tapered column 22 of proximal segment 12 is dimensionally configured for locking engagement with the complimentary female tapered portion of a femoral head component (not shown). One skilled in the art will readily recognize that proximal segment 12 may be constructed to accommodate all styles and materials of femoral head components. An undercut 23 is formed in arm 21 and column 22 on each side of proximal segment 12 to increase the range of motion between neck 20 and the acetabular component (not shown) of a total hip joint replacement system, and to facilitate engagement of a femoral head removal tool (not shown) when it is necessary to disassemble the femoral head from proximal segment 12 during repair or revision of hip prosthesis 10.

Figure 7:
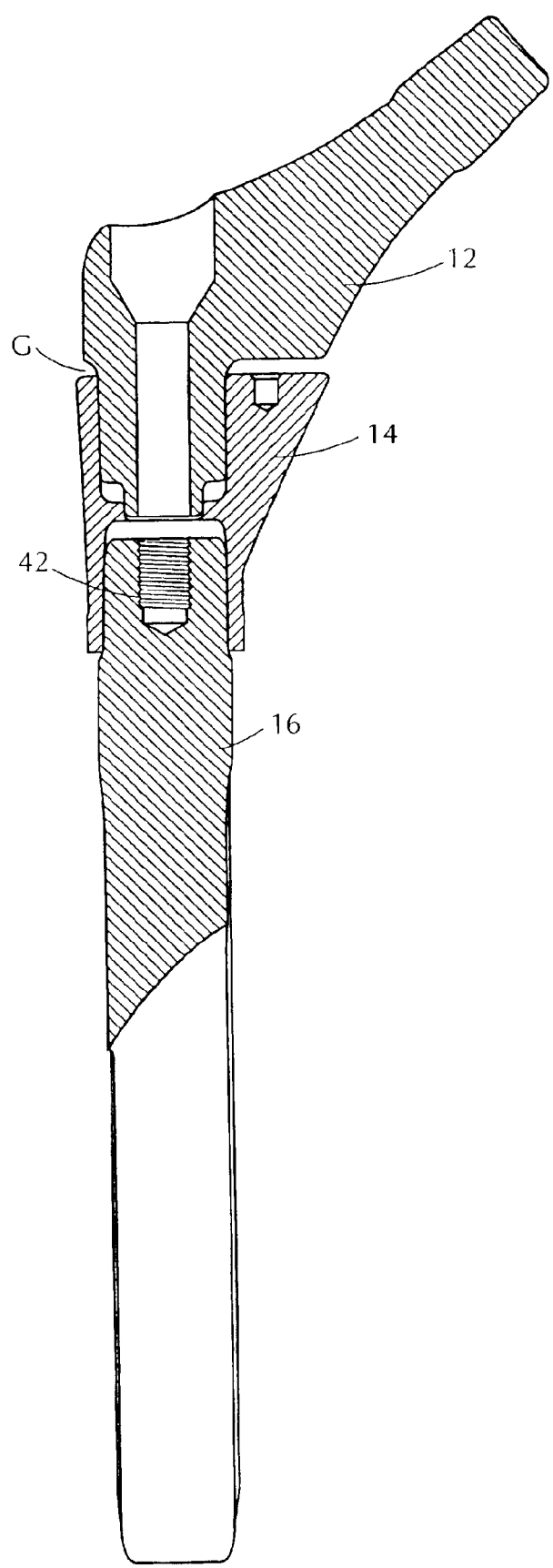
FIG. 7 is a cross-sectional, side elevation view of the engaged proximal, metaphyseal, and distal components of one embodiment of the modular hip prosthesis of the invention.
Figure 8:
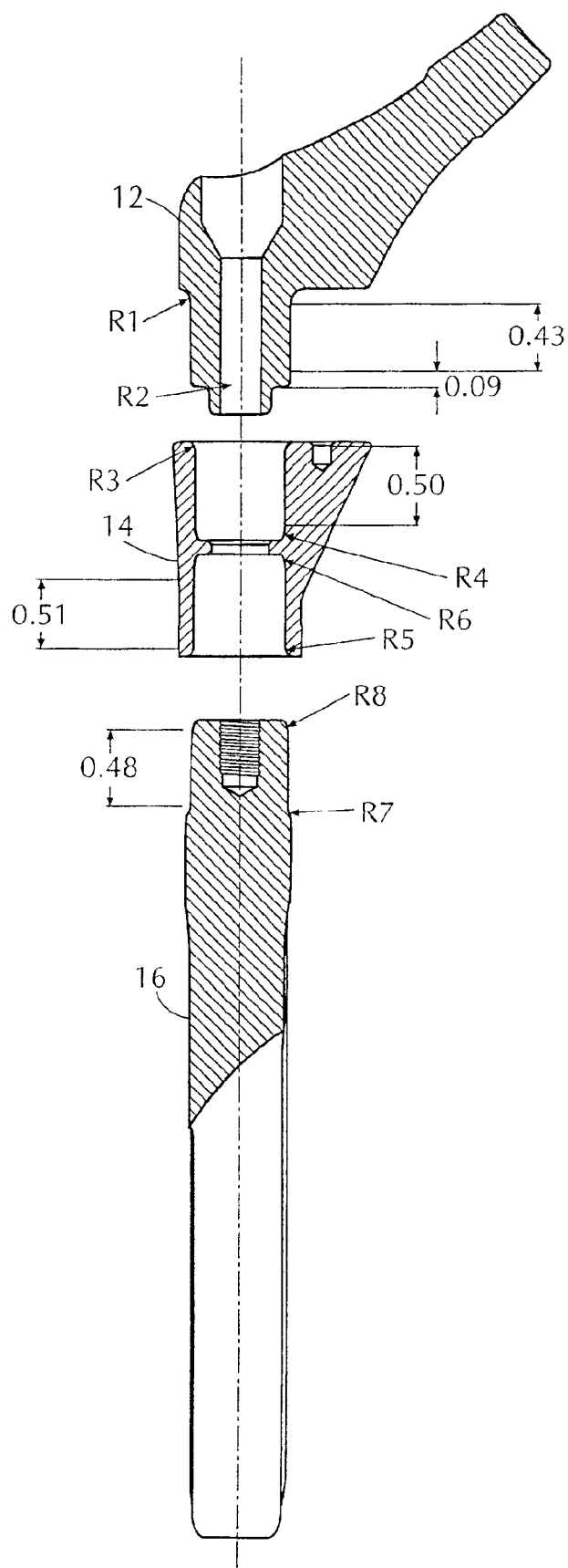
FIG. 8 is a cross-sectional, side elevation view of the proximal, metaphyseal, and distal components of FIG. 7 showing illustrative taper and blend dimensions.

As preferably embodied, tapered portion 25 of extension member 24 comprises a male conical tapered section 25*a* blending into a generally parabolic-shaped male tapered section 25*b* having a blend radius R2 of about 0.25 inch (see FIGS. 2 and 8). The parabolic geometry of tapered section 25*b* decreases the interfacial contact stresses and internal body stresses under bending loading between tapered portion 25 and complementary female tapered portion 33 of metaphyseal segment 14 (described below). As preferably embodied, the conical taper section 25*a* has a taper angle ranging from about 1° to about 2.5° to provide enhanced torsional resistance at the proximal/metaphyseal taper junction. In the illustrative embodiment of the invention shown in FIG. 8, conical tapered section 25*a* has a length of about 0.43 inch, and parabolic tapered section 25*b* has a length of about 0.09 inch. For these illustrative taper lengths, the ratio of parabolic taper length to conical taper length is about 21%. As preferably embodied, the parabolic taper/conical taper length ratio should range from about 5% to about 30%. This range ensures sufficient taper contact area, and minimizes the presence of sharp corners on the parabolic tapered section 25*b* which can lead to high point contact stresses at the proximal/metaphyseal taper junction when the prosthesis is subject to bending stresses. As preferably embodied, the conical tapered section 25*a* has a blend radius R1 of about 0.09 inch (see FIG. 8). The complementary conical tapered section 33*a* of female tapered segment 33 has a blend radius R3 of about 0.05 inch. These differing radii create a reduced stress condition at the proximal/metaphyseal taper junction in the vicinity of gap G (see FIG. 7) that is created when the proximal and metaphyseal segments are joined. Advantageously, the same geometries and radii for tapered portions 25 and 33 can be used for all sizes of proximal segment 12 and metaphyseal segment 14, thereby enhancing size interchangeability, and thus modularity, between the proximal and metaphyseal segments.

As preferably embodied, nipple 26 has a length of about 0.18 inch to increase the moment arm of extension member 24 (see FIGS. 2 and 8), and thereby, assist in unloading the proximal/metaphyseal taper junction upon inducement of bending stresses in the prosthesis. As with the taper geometries and blend radii described above, the same length for nipple 26 can be used for all sizes of proximal segment 12. Nipple 26 is dimensionally configured smaller than the diameter of sections 32*a*, 32*b* and 32*c* of throughbore 32 in metaphyseal segment 14 (described below) so that, when extension member 24 of proximal segment 12 is slidingly received in throughbore 32 upon assembly of the prosthesis components (see FIG. 7 and discussion below), nipple 26 will not initially engage the sidewall of bore 32. Upon application of sufficient load to the femoral head of the prosthesis (not shown), nipple 26 will contact the sidewall of intermediate bore segment 32*b* of bore 32, and thereby, transfer a portion of the induced bending stress away from the proximal/metaphyseal taper junction.

Referring again to FIG. 2, segmented bore 27 of proximal segment 12 includes a first straight section 27*a*, a tapered intermediate section 27*b*, and a second straight section 27*c*. As preferably embodied, section 27*b* tapers inwardly toward bore section 27*c* at an angle of about 60°. Bore sections 27*a*, 27*b* and 27*c* are dimensionally configured to allow screw 18 to pass through proximal segment 12. Bore section 27*a* also acts as a countersink for the head of screw 18, and should be dimensioned large enough to comfortably accommodate a mechanical driver such as a screw driver or drill bit to threadably engage screw 18 with threaded bore 42 formed in distal segment 16 (discussed more fully below) when screw 18 is used as part of the prosthesis 10 assembly.

Figure 3:
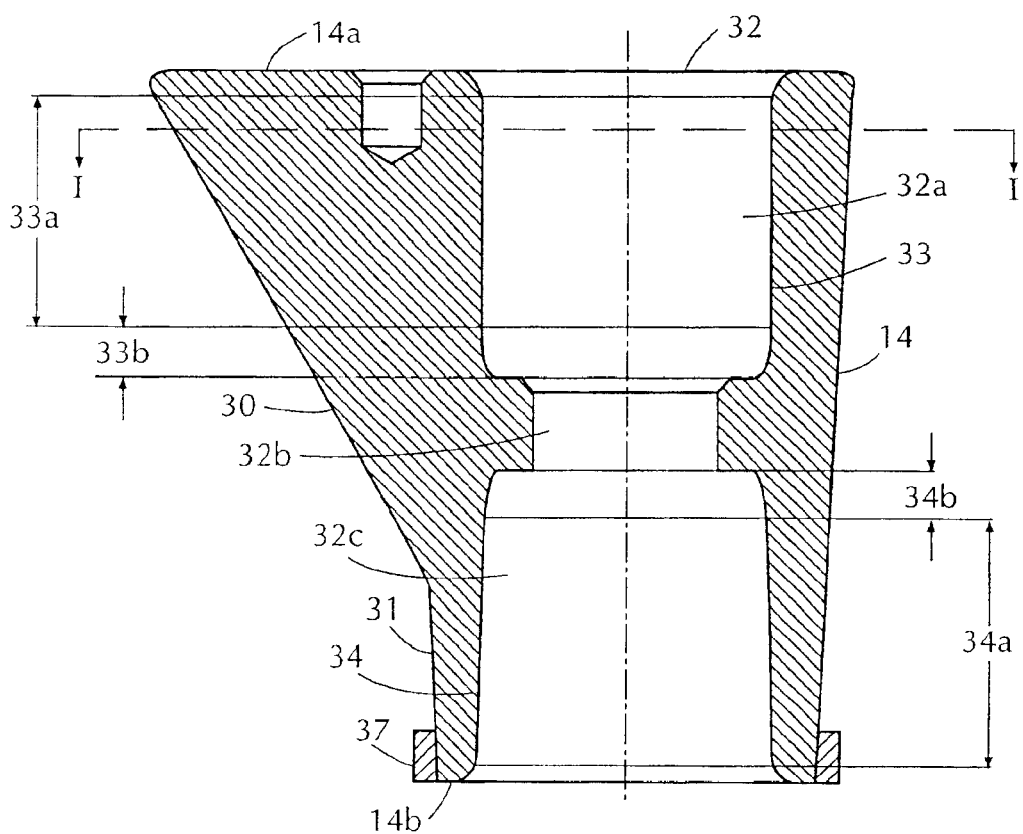
FIG. 3 is a cross-sectional, side elevation view of one embodiment of the metaphyseal component of the invention.
Figure 4:
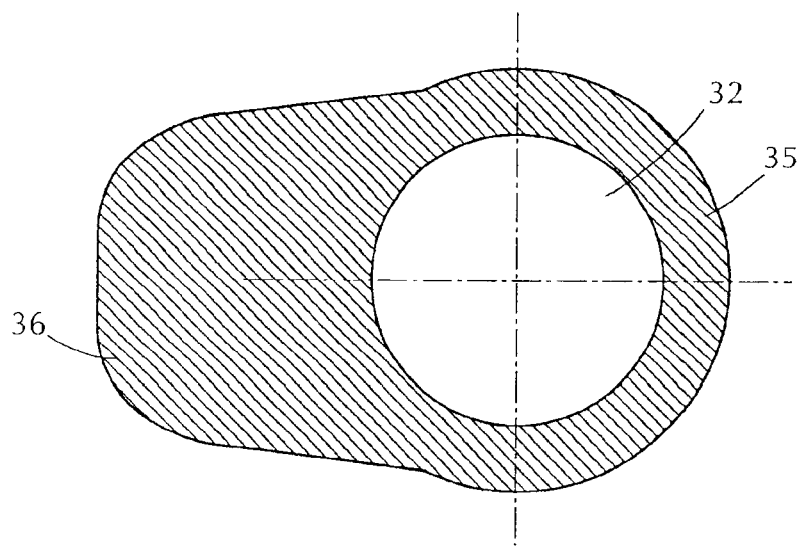
FIG. 4 is a transverse cross-sectional view of one embodiment of the metaphyseal component of the invention taken along lines A—A of FIG. 3.

Referring now to FIG. 3, metaphyseal segment 14 has a proximal end 14*a*, a distal end 14*b*, and is configured with a trapezoidal truncated pyramidal section 30, integrated with a conical section 31. As shown in FIG. 4, this profile presents itself in transverse cross-section as a generally trapezoidal section 36 offset from a generally circular section 35. Alternatively, the pyramidal section 30 may be constructed so that the metaphyseal segment 14 has a generally rectangular transverse cross section offset from a generally circular transverse cross section. Metaphyseal segment 14 is preferably constructed from a biocompatible, high strength titanium alloy, but may also be constructed from other biocompatible materials such as cobalt chrome alloy, stainless steel, and composite materials. Metaphyseal segment 14 also includes a bore 32 comprising proximal bore section 32*a*, intermediate bore section 32*b*, and distal bore section 32*c*. Referring to FIGS. 3 and 8, bore segment 32*a* is formed with a female tapered portion 33 comprising a conical tapered section 33*a* blending into a generally parabolic-shaped tapered section 33*b*. Female tapered sections 33*a* and 33*b* are complementary to male tapered sections 25*a* and 25*b*, respectively, of cylindrical section 24. As here embodied, conical tapered section 33*a* has a taper angle ranging from about 1° to about 2.5°, a length of about 0.50 inch, and a blend radius R3 (referred to above) of about 0.05 inch. Parabolic tapered section 33*b* has a length of about 0.09 inch, and a blend radius R4 of about 0.25 inch (see FIG. 8). For the foregoing illustrative taper lengths, the ratio of parabolic taper length to conical taper length is about 18%.

Tapered sections 33*a* and 33*b* are dimensionally configured to lockingly engage tapered sections 25*a* and 25*b*, respectively, upon insertion of cylindrical section 24 into bore 32. As with tapered sections 25*a* and 25*b* of cylindrical section 24, the parabolic taper/conical taper length ratio for tapered sections 33*a* and 33*b* should range from about 5% to about 30% to ensure reduced contact stresses and internal stresses in the region of the proximal/metaphyseal taper junction. Also, as discussed above with respect to proximal segment 12, the same taper geometries and blend radii for tapered sections 33*a* and 33*b* can be used for all sizes of metaphyseal segment 14 to enhance interchangeability of the proximal and metaphyseal components, and thereby, modularity of the prosthesis 10.

Referring again to FIGS. 3 and 8, bore segment 32*c* of metaphyseal bore 32 is formed with tapered portion 34 comprising a conical tapered section 34*a* and a generally parabolic-shaped tapered section 34*b*. Tapered sections 34*a* and 34*b* are dimensionally configured to lockingly engage the corresponding male tapered sections 43*a* and 43*b* of distal segment 16, respectively, upon insertion of proximal end 16*a* of distal segment 16 into bore 32 of metaphyseal segment 14 (as more fully discussed below). As here embodied, the conical tapered section 34*a* has a length of about 0.51 inch, a taper angle ranging from about 1° to about 2.5°, and a blend radius R5 of about 0.50 inch. Parabolic tapered section 34*b* has a length of about 0.09 inch and a blend radius R6 of about 0.25 inch (see FIG. 8). For the foregoing illustrative taper lengths, the ratio of parabolic taper length to conical taper length is about 18%. As with the other tapered portions of the prosthesis 10 discussed above, the parabolic taper/conical taper length ratio should range from about 5% to about 30% to ensure sufficient taper contact area and minimize high point contact stresses at the proximal/metaphyseal taper junction. Also, as with the other tapered portions described above, the same taper geometries and blend radii for tapered sections 34*a* and 34*b* can be used for all sizes of metaphyseal segment 14 to enhance interchangeability of components, and thereby, modularity of the prosthesis 10.

The geometry of metaphyseal segment 14 increases torsional stability of the component during use in the body, and provides better fill of the proximal intramedulary canal. The outer surface finish of metaphyseal segment 14 may be polished, with a surface roughness average of about 32 microinches or less as determined by profilometry. The outer surface finish may also be smooth matte or machined using surface preparation techniques well known in the art. As preferably embodied, the outer surface of metaphyseal segment 14 contains a bone engaging surface coating, such as, for example, grit blasted surface, plasma spray coating, sintered metal bead coating, hydroxylapatite coating, or other bioactive coatings such as bio-glass ceramics, demineralized bone and carrier, and growth factor and carrier. The application of such coatings to metallic implant surfaces is well known in the art. Optionally, metaphyseal segment 14 may be constructed with a distal ring 37. Distal ring 37 is a region of raised material equal in thickness to the minimum thickness of the bone engaging coating applied to the outer surface of the metaphyseal segment. Distal ring 37 increases the wall thickness of conical section 31 of metaphyseal segment 14. This in turn will increase the fatigue strength of conical section 31 by increasing the local wall thickness and shielding it from notches that may result from the porous coating process. As preferably embodied, distal ring 37 should be used in smaller sizes of metaphyseal segment 14, wherein the sidewall of conical section 31 in the vicinity of distal end 14*b* may be relatively thin. The local stress levels on conical section 31 that may necessitate use of distal ring 37 for a particular size of metaphyseal segment 14 can be readily determined by persons skilled in the art.

Figure 5:
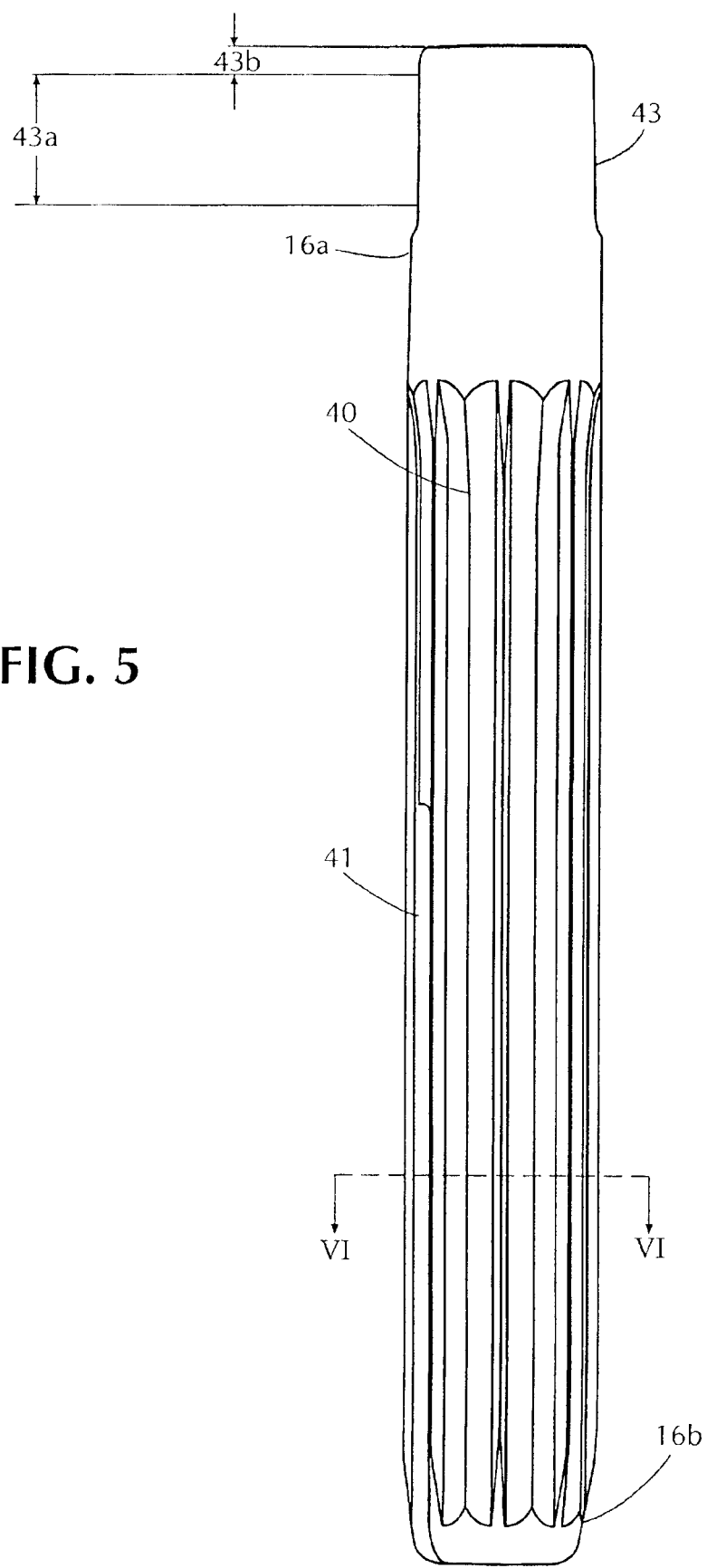
FIG. 5 is a cross-sectional, side elevation view of one embodiment of the distal component of the invention.

Referring now to FIG. 5, distal segment 16 is formed with a proximal end 16*a*, a distal tip 16*b*, and includes a plurality of sharpened longitudinal flutes 40 formed along an incremental length of the outer surface thereof. The sharp edges of flutes 40 dig into the cortical bone wall of the intramedulary canal to increase the torsional stability of distal segment 16 during use of the prosthesis in the body. Distal segment 16 is also optionally formed with a coronal slot 41 beginning at distal tip 16*b*, and proceeding proximally for an incremental length thereof. Coronal slot 41 increases the flexibility of distal segment 16. This increased flexibility inhibits the concentration of stresses at distal tip 16*b* when the prosthesis is loaded, and allows the prosthesis to better accommodate the curvature of the intramedullary canal. Those skilled in the art will recognize that the length of longitudinal flutes 40 can readily be adjusted as desired, in light of the overall prosthesis design scheme, to facilitate resistance to torsional loadings on the prosthesis. In the illustrative embodiment of distal segment 16 shown in the Figures, the length of longitudinal flutes 40 is about 80% of the overall length of distal segment 16. Advantageously, the same ratio of flute length to distal segment length can be used for all sizes of distal segment 16. Those skilled in the art will also recognize that the length of coronal slot 41 can be readily adjusted to provide the desired degree of flexibility in distal segment 16 without unduly compromising the fatigue strength of the distal segment.

Figure 6:
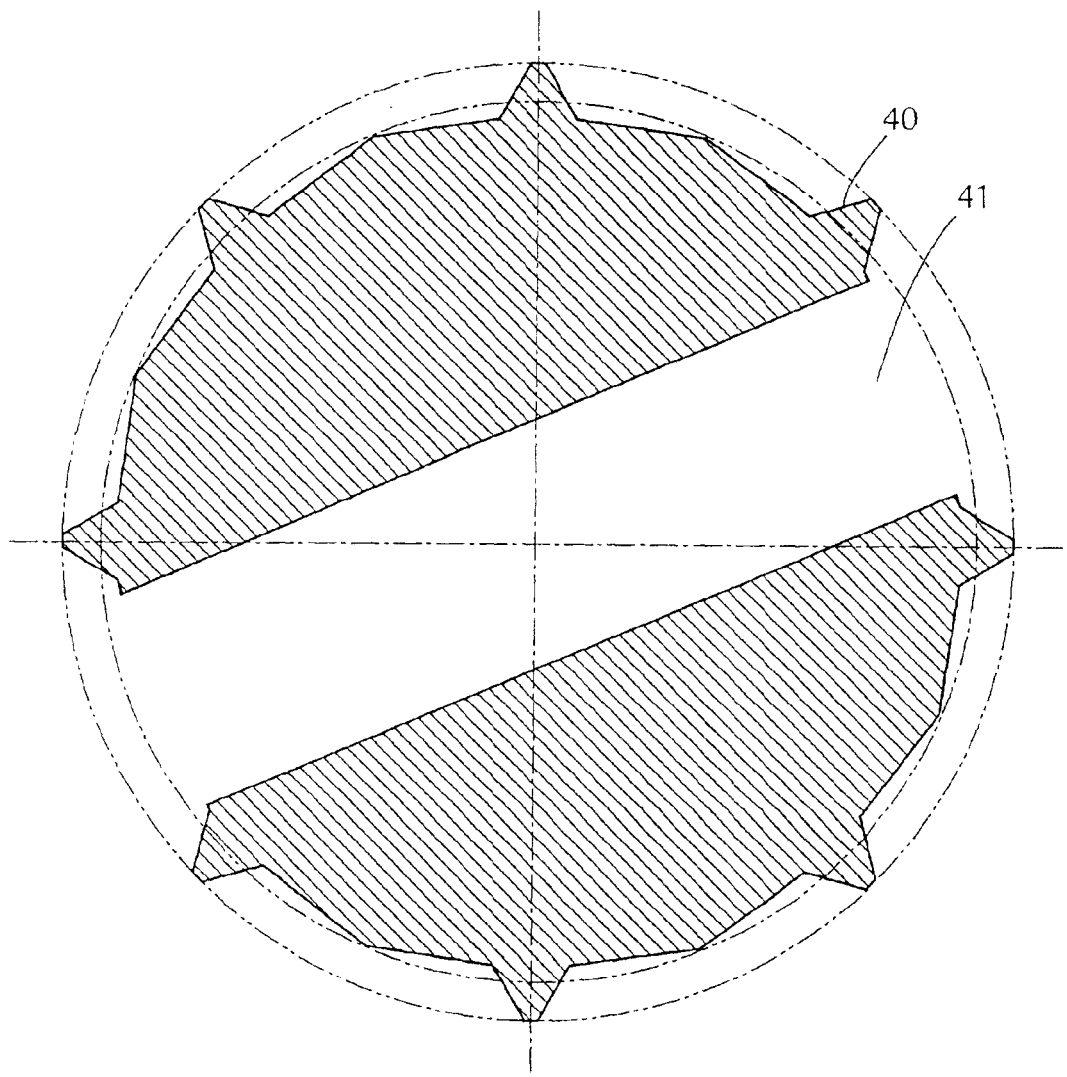
FIG. 6 is a transverse cross-sectional view of one embodiment of the distal component of the invention taken along lines B—B of FIG. 5.

As preferably embodied, distal tip 16*b* has a generally parabolic axial cross-section which also serves to reduce contact stresses between distal segment 16 and the bone in the vicinity of the distal tip. As shown in FIG. 6, distal segment 16 has a generally round transverse cross-section, but may be constructed with other cross-sectional geometries such as, for example, hexagonal or oval. Optionally, distal segment 16 may be formed with longitudinal channels instead of sharp longitudinal flutes to facilitate both increased stem flexibility and engagement of cortical bone in the intramedulary canal. Although distal segment 16 shown in the Figures has a straight profile, it may also be curved to better match the natural curvature of the patient's intramedulary canal. Distal segment 16 is preferably constructed from a biocompatible, high strength titanium alloy, but may also be constructed from other biocompatible materials such as cobalt chrome alloy, stainless steel, and composite materials. Further, distal segment 16 is preferably provided with a polished outer surface finish having a surface roughness average of 32 microinches or less as determined by profilometry. The distal segment may also be provided with a smooth matte or machined outer surface finish using surface preparation techniques well known in the art. To facilitate fixation of distal segment 16 to the cortical bone wall of the intramedullary canal, if desired, distal segment 16 may also be constructed without longitudinal flutes, and instead provided with a porous bone engaging surface coating, such as, for example, grit blasted surface, plasma spray coating, sintered metal bead coating, hydroxylapatite coating, or other bioactive coating such as bio-glass ceramics, deminerealized bone and carrier, and growth factor and carrier.

Referring now to FIGS. 5 and 8, distal segment 16 is also formed with a threaded bore 42 adjacent proximal end 16*a* thereof. Bore 42 is dimensionally configured to threadably engage screw 18 upon insertion through the aligned bores of proximal segment 12, metaphyseal segment 14, and distal segment 16 (see discussion below). Distal segment 16 is also formed with a male tapered portion 43 adjacent proximal end 16a. Tapered segment 43 comprises a conical tapered section 43a and a generally parabolic-shaped tapered section 43b. Male tapered sections 43a and 43b are dimensionally configured to lockingly engage the corresponding female tapered sections 34a and 34b of metaphyseal segment 14, respectively, upon insertion of proximal end 16a of distal segment 16 into bore 32 of metaphyseal segment 14. As here embodied, conical tapered section 43a has a length of about 0.48 inch, a taper angle ranging from about 1° to about 2.5°, and a blend radius R7 of about 0.09 inch. Parabolic tapered section 43b has a length of about 0.09 inch, and a blend radius R8 of about 0.25 inch (see FIG. 8). For the foregoing illustrative taper lengths, the ratio of parabolic taper length to conical taper length is about 19%. The parabolic/conical taper length ratio should range from about 5% to about 30% to ensure sufficient taper contact area and minimize high point contact stresses at the metaphyseal/distal taper junction. Also, as with the other tapered portions described above, the same taper geometries and blend radii for tapered sections 43a and 43b can be used for all sizes of distal segment 16 to enhance interchangeability of the distal and metaphyseal components, and thereby, modularity of the prosthesis 10.

Referring now to FIGS. 7 and 8, cross-sectional views of proximal segment 12, metaphyseal segment 14, and distal segment 16 are shown to more clearly illustrate the internal relationship between these components upon assembly. As shown in the Figures, extension member 24 of proximal segment 12 is received in close-fitting, sliding relationship in bore section 32a of metaphyseal segment 14, with tapered sections 25a and 25b of extension 24 lockingly engaging tapered sections 33a and 33b of bore segment 32a, respectively. Similarly, proximal end 16a of distal segment 16 is received in close-fitting, sliding relationship in bore segment 32c of metaphyseal segment 14, with tapered sections 43a and 43b of distal segment 16 lockingly engaging tapered sections 34a and 34b of bore segment 32c, respectively. Before a taper lock relationship is established between proximal segment 12 and metaphyseal segment 14, the angular orientation of arm 21 and column 22 of proximal segment 12 is established to place column 22 in the desired position to receive a conventional femoral head component (not shown). Upon locking engagement of the complimentary tapered portions of the proximal, metaphyseal and distal segments, bores 27, 32, and 42 will be in axial alignment. Thereupon, screw 18 is inserted through the aligned bores into threaded engagement with the complimentary threaded section of bore 42. Screw 18 has a countersunk head 19 receivable in countersink 28 formed in section 27a of metaphyseal bore 27. Screw 18 is securely tightened to further enhance locking engagement of the proximal, metaphyseal and distal segments if desired.

The present invention may be embodied in other forms than disclosed in the detailed description of the invention without departing from the spirit or essential characteristics of the invention. Accordingly, the described embodiments of the invention are to be considered in all respects as illustrative and not restrictive. The scope of the present invention is therefore indicated by the claims set forth below, and not by the foregoing description of the invention. All modifications which come within the meaning and range of equivalency of the claimed subject matter are to be embraced within the scope of the claims.

What is claimed is:
1. A modular hip prosthesis, comprising:
a proximal segment, said proximal segment including a neck lockingly engageable with a femoral head component, said proximal segment further including a male tapered portion extending distally of said neck;
a distal segment having a proximal end and a distal tip, said distal segment including a male tapered portion adjacent said proximal end thereof;
a metaphyseal segment having a proximal end and a distal end, said metaphyseal segment including a bone engaging outer surface portion, said metaphyseal segment further including an axial bore therethrough, said axial bore including first and second female tapered portions, said first female tapered portion located adjacent to said proximal end of said metaphyseal segment and dimensionally configured to lockingly engage said male tapered portion of said proximal segment, said second female tapered portion located adjacent to said distal end of said metaphyseal segment and dimensionally configured to lockingly engage said male tapered portion of said distal segment;
wherein said proximal segment further includes an axial bore therethrough, said proximal segment engageable with said proximal end of said metaphyseal segment to align said axial bores formed through said proximal and metaphyseal segments, said distal segment further including a threaded axial bore adjacent said proximal end thereof, said proximal end of said distal segment engageable with said distal end of said metaphyseal segment to align said axial bores formed through said distal and metaphyseal segments, said modular hip prosthesis further comprising a screw dimensionally configured to pass through said aligned bores of said proximal, metaphyseal and distal segments and into threaded engagement with said threaded axial bore of said distal segment;
wherein said distal segment includes a bone engaging outer surface portion; and
wherein the distal tip of said distal segment has a generally parabolic axial cross section.
2. A modular hip prosthesis, comprising:
a proximal segment, said proximal segment including a neck lockingly engageable with a femoral head component, said proximal segment further including a male tapered portion extending distally of said neck:
a distal segment having a proximal end and a distal tip, said distal segment including a male tapered portion adjacent said proximal end thereof;
a metaphyseal segment having a proximal end and a distal end, said metaphyseal segment including a bone engaging outer surface portion, said metaphyseal segment further including an axial bore therethrough, said axial bore including first and second female tapered portions, said first female tapered portion located adjacent to said proximal end of said metaphyseal segment and dimensionally configured to lockingly engage said male tapered portion of said proximal segment, said second female tapered portion located adjacent to said distal end of said metaphyseal segment and dimensionally configured to lockingly engage said male tapered portion of said distal segment;
wherein said proximal segment further includes an axial bore therethrough, said proximal segment engageable with said proximal end of said metaphyseal segment to align said axial bores formed through said proximal and metaphyseal segments, said distal segment further including a threaded axial bore adjacent said proximal end thereof, said proximal end of said distal segment engageable with said distal end of said metaphyseal segment to align said axial bores formed through said distal and metaphyseal segments, said modular hip prosthesis further comprising a screw dimensionally configured to pass through said aligned bores of said proximal, metaphyseal and distal segments and into threaded engagement with said threaded axial bore of said distal segment;

wherein said distal segment includes a bone engaging outer surface portion; and wherein said male tapered portion of said distal segment and said second female tapered portion of said metaphyseal segment each comprise a conical tapered section blending into a generally parabolic section.

3. The modular hip prosthesis of claim 2, wherein the ratio of parabolic taper length to conical taper length ranges from about 5% to about 30%.

4. The modular hip prosthesis of claim 3, wherein the taper angle of said conical tapered sections of said distal segment and said second female tapered portion of said metaphyseal segment ranges from about 1° to about 2.5°.

5. A modular hip prosthesis, comprising:

a proximal segment, said proximal segment including a neck lockingly engageable with a femoral head component, said proximal segment further including a male tapered portion extending distally of said neck;

a distal segment having a proximal end and a distal end, said distal segment including a male tapered portion adjacent said proximal end thereof;

a metaphyseal segment having a proximal end and a distal end, said metaphyseal segment including a bone engaging outer surface portion, said metaphyseal segment further including an axial bore therethrough, said axial bore including first and second female tapered portions, said first female tapered portion located adjacent to said proximal end of said metaphyseal segment and dimensionally configured to lockingly engage said male tapered portion of said proximal segment, said second female tapered portion located adjacent to said distal end of said metaphyseal segment and dimensionally configured to lockingly engage said male tapered portion of said distal segment;

wherein said proximal segment further includes an axial bore therethrough, said proximal segment engageable with said proximal end of said metaphyseal segment to align said axial bores formed through said proximal and metaphyseal segments, said distal segment further including a threaded axial bore adjacent said proximal end thereof, said proximal end of said distal segment engageable with said distal end of said metaphyseal segment to align said axial bores formed through said distal and metaphyseal segments, said modular hip prosthesis further comprising a screw dimensionally configured to pass through said aligned bores of said proximal, metaphyseal and distal segments and into threaded engagement with said threaded axial bore of said distal segment;

wherein said distal segment includes a bone engaging outer surface portion; and wherein said male tapered portion of said proximal segment and said first female tapered portion of said metaphyseal segment each comprise a conical tapered section blending into a generally parabolic section.

6. The modular hip prosthesis of claim 5, wherein the ratio of parabolic taper length to conical taper length ranges from about 5% to about 30%.

7. The modular hip prosthesis of claim 6, wherein the taper angle of said conical tapered sections of said proximal segment and said first female tapered portion of said metaphyseal segment ranges from about 1° to about 2.5°.

8. A modular hip prosthesis, comprising:

a proximal segment, said proximal segment including a neck lockingly engageable with a femoral head component, said proximal segment further including a male tapered portion extending distally of said neck;

a distal segment having a proximal end and a distal tip, said distal segment including a male tapered portion adjacent said proximal end thereof;

a metaphyseal segment having a proximal end and a distal end, said metaphyseal segment including a bone engaging outer surface portion, said metaphyseal segment further including an axial bore therethrough, said axial bore including first and second female tapered portions, said first female tapered portion located adjacent to said proximal end of said metaphyseal segment and dimensionally configured to lockingly engage said male tapered portion of said proximal segment, said second female tapered portion located adjacent to said distal end of said metaphyseal segment and dimensionally configured to lockingly engage said male tapered portion of said distal segment;

wherein said proximal segment further includes an axial bore therethrough, said proximal segment engageable with said proximal end of said metaphyseal segment to align said axial bores formed through said proximal and metaphyseal segments, said distal segment further including a threaded axial bore adjacent said proximal end thereof, said proximal end of said distal segment engageable with said distal end of said metaphyseal segment to align said axial bores formed through said distal and metaphyseal segments, said modular hip prosthesis further comprising a screw dimensionally configured to pass through said aligned bores of said proximal, metaphyseal and distal segments and into threaded engagement with said threaded axial bore of said distal segment;

wherein said distal segment includes a bone engaging outer surface portion; and wherein said metaphyseal segment has a trapezoidal truncated pyramidal section integrated with a generally conical section.

9. The modular hip prosthesis of claim 8, wherein said metaphyseal segment has a generally trapezoidal transverse cross section offset from a generally circular transverse cross section.

10. The modular hip prosthesis of claim 8, wherein said metaphyseal segment includes an outer ring formed around at least a portion of said generally conical section.

11. A modular hip prosthesis, comprising:

a proximal segment having an axial bore therethrough, said proximal segment including a neck lockingly engageable with a femoral head component, said proximal segment further including a male tapered portion extending distally of said neck;

a distal segment having a proximal end and a distal tip, said distal segment formed with a threaded axial bore adjacent to said proximal end thereof, said distal segment further formed with a male tapered portion adjacent said proximal end thereof; and a metaphyseal segment having a proximal end and a distal end, said metaphyseal segment including a bone engaging outer surface portion, said metaphyseal segment further including an axial bore therethrough, said axial bore including first and second female tapered portions, said first female tapered portion located adjacent said proximal end of said metaphyseal segment and dimensionally configured to lockingly engage said male tapered portion of said proximal segment, said second female tapered portion located adjacent said distal end of said metaphyseal segment and dimensionally configured to lockingly engage said male tapered portion of said distal segment;

said proximal segment engageable with said proximal end of said metaphyseal segment to align said axial bores formed through said proximal and metaphyseal segments, said proximal end of said distal segment engageable with said distal end of said metaphyseal segment to align said axial bores formed through said distal and metaphyseal segments; and said modular hip prosthesis further comprising a screw dimensionally configured to pass through said aligned bores of said proximal, metaphyseal and distal segments and into threaded engagement with said threaded axial bore of said distal segment;

wherein said male tapered portion of said proximal segment is formed on an extension member extending distally of said neck; and wherein said extension member includes a nipple member extending distally thereof.

12. The modular hip prosthesis of claim 11, wherein said male tapered portion of said proximal segment and said first female tapered portion of said metaphyseal segment each comprise a conical tapered section blending into a generally parabolic section.

13. The modular hip prosthesis of claim 12, wherein the ratio of parabolic taper length to conical taper length ranges from about 5% to about 30%.

14. The modular hip prosthesis of claim 13, wherein the taper angle of said conical sections of said proximal segment and said first female tapered portion of said metaphyseal segment ranges from about 1° to about 2.5°.

15. The modular hip prosthesis of claim 11, wherein said proximal segment is constructed from a material selected from the group consisting of titanium metal alloy, cobalt chromium alloy, and stainless steel.

16. The modular hip prosthesis of claim 11, wherein said distal segment further includes longitudinal flutes along an incremental length thereof.

17. The modular hip prosthesis of claim 11, wherein said distal segment further includes a coronal slot formed along an incremental length thereof.

18. The modular hip prosthesis of claim 11, wherein said male tapered portion of said distal segment and said second female tapered portion of said metaphyseal segment each comprise a conical tapered section blending into a generally parabolic section.

19. The modular hip prosthesis of claim 18, wherein the ratio of parabolic taper length to conical taper length ranges from about 5% to about 30%.

20. The modular hip prosthesis of claim 19, wherein the taper angle of said conical tapered sections of said distal segment and said second female tapered section of said metaphyseal segment ranges from about 1° to about 2.5°.

21. The modular hip prosthesis of claim 11, wherein said distal segment is constructed from a material selected from the group consisting of titanium metal alloy, cobalt chromium alloy, and stainless steel.

22. The modular hip prosthesis of claim 11, wherein said distal segment includes a bone engaging outer surface selected from the group consisting of grit blasted surface, sintered metal bead coating, hydroxylapatite coating, plasma spray coating, bio-glass ceramic coating, demineralized bone and carrier, and growth factor and carrier.

23. The modular hip prosthesis of claim 11, wherein said metaphyseal segment has a trapezoidal truncated section integrated with a generally conical section.

24. The modular hip prosthesis of claim 23, wherein said metaphyseal segment has a generally trapezoidal transverse cross section offset from a generally circular cross section.

25. The modular hip prosthesis of claim 23, wherein said metaphyseal segment includes an outer ring formed around at least a portion of said generally conical section.

26. The modular hip prosthesis of claim 11, wherein said bone engaging surface of said metaphyseal segment is selected from the group consisting of grit blasted surface, sintered metal bead coating, hydroxylapatite coating, plasma spray coating, bio-glass ceramic coating, demineralized bone and carrier, and growth factor and carrier.

27. The modular hip prosthesis of claim 11, wherein said metaphyseal segment is constructed from a material selected from the group consisting of titanium metal alloy, cobalt chromium alloy, and stainless steel.

* * * * *